United States Patent
Cho (10) Patent No.: US 7,762,972 B2
(45) Date of Patent: Jul. 27, 2010

(54) ORTHOPEDIC KNEE JOINT BRACE

(75) Inventor: Sang deog Cho, Seoul (KR)

(73) Assignee: Davincimeditec Co., Ltd. (KR)

( * ) Notice: Subject to any disclaimer, the term of this patent is extended or adjusted under 35 U.S.C. 154(b) by 33 days.

(21) Appl. No.: 12/159,985

(22) PCT Filed: Dec. 18, 2006

(86) PCT No.: PCT/KR2006/005527

§ 371 (c)(1), (2), (4) Date: Jul. 2, 2008

(87) PCT Pub. No.: WO2007/081095

PCT Pub. Date: Jul. 19, 2007

(65) Prior Publication Data

US 2009/0018476 A1   Jan. 15, 2009

(30) Foreign Application Priority Data

Jan. 9, 2006   (KR)   ............... 10-2006-0002118

(51) Int. Cl.
*A61F 5/00* (2006.01)
*F16C 11/00* (2006.01)
(52) U.S. Cl. ............... 602/16; 403/119; 403/144
(58) Field of Classification Search ............... 602/26, 602/23, 5, 1, 16; 128/846, 869, 882; 403/52, 403/119, 122, 128, 129, 144
See application file for complete search history.

(56) References Cited

U.S. PATENT DOCUMENTS

| 3,826,251 A * | 7/1974 | Ross ............... 602/16 |
| 2004/0054311 A1* | 3/2004 | Sterling ............... 602/26 |
| 2004/0097859 A1* | 5/2004 | Stearns ............... 602/26 |

FOREIGN PATENT DOCUMENTS

| KR | 20-0390002 | 7/2005 |
| KR | 1020060001381 | 1/2006 |

* cited by examiner

*Primary Examiner*—Patricia M Bianco
*Assistant Examiner*—Tarla R Patel
(74) *Attorney, Agent, or Firm*—Park & Associates IP Law LLC (57) ABSTRACT

Disclosed herein is an orthopedic knee joint brace, which permits smooth knee exercise, increases the durability of a spring, and ensures structural rigidity in a shock absorbing operation. To this end, the orthopedic knee joint brace includes an upper cuff assembly (100) having an anatomical shape of a thigh to support the thigh, and a lower cuff assembly (200) provided under the upper cuff assembly and spaced apart from the upper cuff assembly. The orthopedic knee joint brace includes a pair of damping pivot assemblies (300) coupling facing ends of both sides of the upper and lower cuff assemblies to each other. Each of the damping pivot assemblies has a multiple pivot link structure and a guide damping structure to correspond to the movement of the knee joint.

4 Claims, 10 Drawing Sheets

ORTHOPEDIC KNEE JOINT BRACE

TECHNICAL FIELD

The present invention relates, in general, to an orthopedic knee joint brace and a using method thereof and, more particularly, to an orthopedic knee joint brace and a using method thereof, intended to stabilize and adjust the knee joint of a human body, which suffers pain, is to be corrected, or requires the use of a knee joint brace, due to diseases or injuries or for congenital reasons.

Generally, an orthopedic knee joint brace or protector is used by a patient who has had his or her knee joint operated on or is undergoing orthopedic treatment, a disabled person, or an old or weak person, and is worn on the knee or the area around the knee.

Such a knee joint brace has been devised to control and stabilize the lateral movement of the knee joint, to restrict or correct the flexion of the joint, and to prevent injuries to the knee from recurring, through a general control method.

For example, the knee joint brace may be used to delay the progress of knee arthritis and relieve the pain of knee arthritis. Here, knee arthritis is irritation which is caused when cartilage forming the knee loses resilience and thus loses its ability to protect the joint from external shocks. This irritation causes severe pain due to the loading of a person's body weight as a result of gravity and due to friction of the damaged knee joint.

Meanwhile, an orthopedic knee joint brace, which simply has on both sides thereof cuffs or has a simple hinge part, promotes blood circulation and eliminates the need to be frequently put on, thus solving the problems of a knee protector which is made of elastic fiber and merely performs compression.

However, the orthopedic knee joint brace is problematic in that it is relatively inflexible, so that the movement of the knee joint and leg is limited when a user walks or goes up stairs. Particularly, the orthopedic knee joint brace is unable to mitigate friction and shocks acting on the knee joint due to gravity as soon as a user steps on the ground.

BACKGROUND ART

Figure 1:
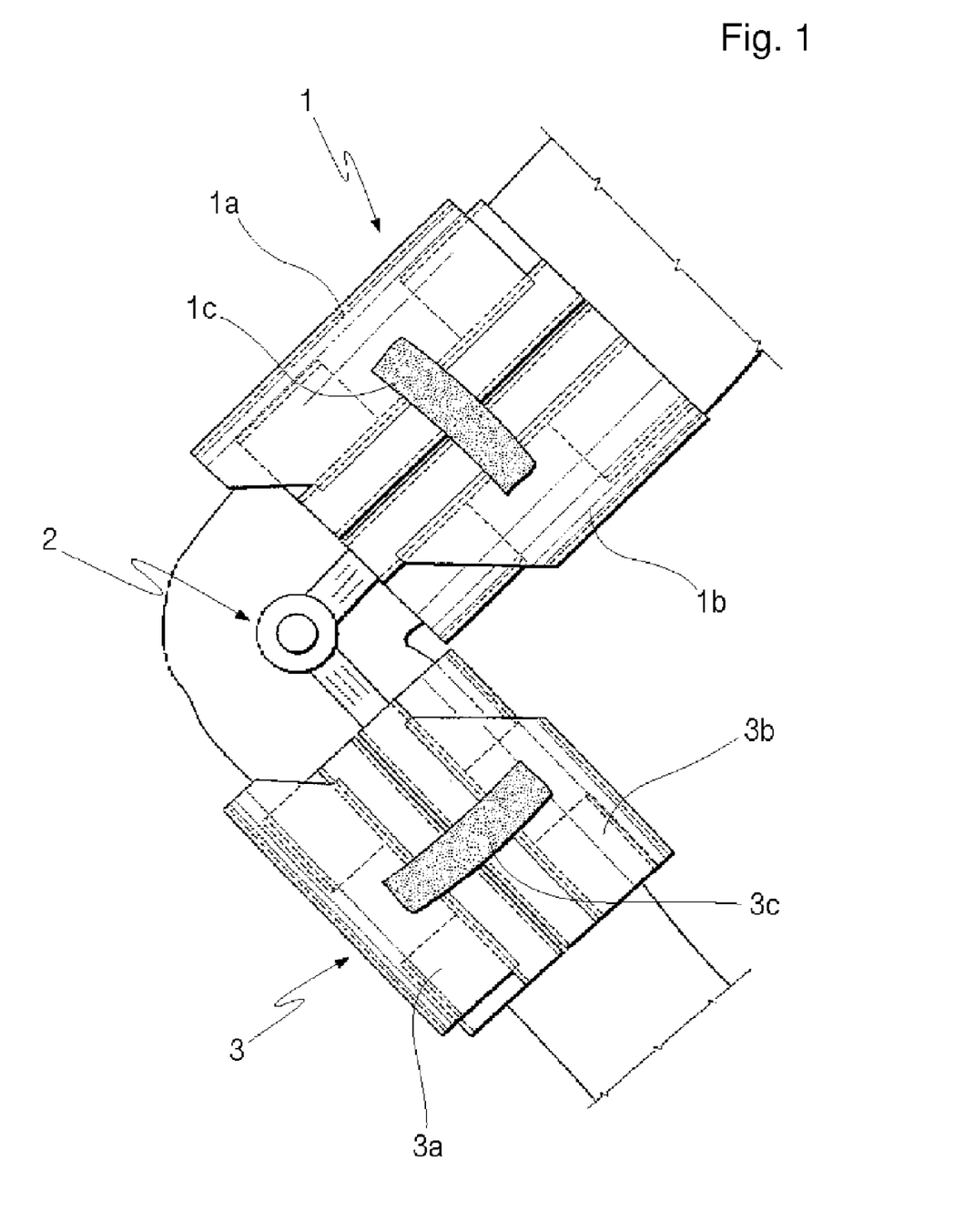
FIG. 1 is a side view illustrating a conventional knee brace.

In order to solve the problems, U.S. Pat. No. 5,707,347, which was registered in 1998, has been proposed. As shown in FIG. 1, the impact-dispersing knee brace of the cited document includes an upper cuff 1, a lower cuff 3, and a support 2. The upper cuff includes arcuate anterior and posterior segments 1a and 1b, which are fastened to the thigh region surrounding the thighbone of the leg, and a coupling band 1c which couples the anterior and posterior segments to each other. The lower cuff includes anterior and posterior segments 3a and 3b, which are fastened to the calf region surrounding the shinbone of the leg, and a coupling band 3c, which couples the anterior and posterior segments to each other. The support comprises a pair of arms between the upper cuff 1 and the lower cuff 3, and is operated in the manner of a hinge.

The hinge-operating support 2 is connected at both ends thereof to the upper cuff 1 and the lower cuff 3. A spring is provided at each of the connecting points to elastically bias the support 2, thus dispersing the impact of the knee joint to the upper cuff 1 and the lower cuff 3.

However, such a conventional impact-dispersing knee brace has a drawback in that it does not consider the anatomical shape of the human body and in that the hinge-operating support is provided between the upper cuff and the lower cuff, so that it is very inconvenient to bend or stretch the joint in response to the motion of the body. Further, the conventional impact-dispersing knee brace has no adjusting means for compensating for imbalance between the left and right sides of cartilage, so that it is impossible to relieve a patient's knee pain.

In order to solve the problems, Korean U.M. Registration No. 0378573 has been proposed, which was filed by the applicant of this invention and is entitled 'Knee Protection and Impact Relief Device for Knee Protection Brace'.

According to U.M. Registration No. 0378573, the device includes a tubular body, an upper cuff, a lower cuff, a movable pin, a hinge, and a spring. The tubular body has on an upper portion thereof an upper opening. The tubular body has on a lower portion thereof a lower opening, so that supporting plates of the lower cuff are integrated with the body. A hole is formed in the central portion of the tubular body, and a semi-circular moving slot is formed at a position around the hole. The upper cuff has a ring, which is provided on the lower surface of the upper cuff, which is retractably inserted into the upper opening of the tubular body. The lower cuff has the plurality of integrated supporting plates. Each of the supporting plates has on an upper portion thereof a moving slot, and has a hole under the moving slot, so that the lower cuff is inserted into the lower opening of the tubular body. A rotary part is provided on the central portion of the lower cuff. The movable pin is movably inserted into the moving slot of the lower cuff and the moving slot of the tubular body, which are aligned with each other. The hinge is inserted into the hole of the lower cuff and the hole of the tubular body, which are aligned with each other. The spring is inserted into the tubular body. One end of the spring is coupled to the ring of the upper cuff, while the other end of the spring is coupled to the moving slot of the lower cuff.

According to U.M. Registration No. 0378573, in order to minimize friction and impact acting on the knee cartilage due to a user's body weight, the thighbone and the shinbone are pulled away from the cartilage so that a small load acts on the cartilage even when the foot contacts the ground. However, according to the bend angle of the knee, the elastic force of the spring varies. That is, as the elastic force is increased, the thighbone is efficiently pushed up. As a result, the user must bend his or her knee as much as possible when he or she walks, thus causing inconvenience.

Further, unless the lower cuff is firmly secured to the shinbone region (e.g.: the calf region), when the upper cuff secured to the thighbone region (e.g.: the inguinal region) is pushed up by the elastic force or the restoring force of the spring, the lower cuff is pushed down. Thus, the device may undesirably slide down from the knee. In order to overcome this problem, if the lower cuff is too firmly secured to the shinbone region, it hinders the blood circulation of the leg. Therefore, it is impossible to wear the device for a lengthy period of time.

In order to solve the problems, Korean Patent Appln. No. 10-2005-0032044 was proposed by the applicant of this invention. According to the cited document, a knee joint brace relieves pain and impact acting on the knee joint using a spring and a cam when the knee is extended.

According to Korean Patent Appln. No. 10-2005-0032044, an upper cuff secured to the thighbone region is shaped so that its upper portion is wide and its lower portion is narrow, and a lower cuff secured to the shinbone region is shaped so that its upper portion is narrow and its lower portion is wide, thus reliably tightening the upper and lower portions of the leg. The knee joint brace includes the upper cuff, which performs a vertical motion using a compression means that is pushed up by the rotating movement of the lower cuff, and a tubular body which engages with a cam shaft of the lower cuff, which is inserted into the open lower end of the tubular body, and accommodates the upper cuff, which is inserted into the open upper end of the tubular body.

However, according to Korean Patent Appln. No. 10-2005-0032044, one hinge or the cam shaft, such as a pivot point, is placed on the extrapolated line of the rotating motion of the knee. When the cam rotates about the cam shaft in the tubular body, a spring, coupled to a silicone plate, contracts, so that the upper cuff is pushed up.

However, the prior art disclosed in Korean Patent Appln. No. 10-2005-0032044 is problematic in that a large load acts on the cam and the rotation of the cam is not converted into a vertical stroke (linear moving distance for moving the upper cuff up) because of the shape and structure of the cam, so that the natural rotation of the knee is hindered and it is difficult to secure rigidity due to the shape of the cam.

Further, according to the prior art, when a flat silicone plate compresses the spring, slipping or unnatural operation may occur, and a lot of sliding noise is generated. Thus, it is difficult to perform a smooth shock absorbing action.

Further, when cartilage wears out due to specific diseases (e.g.: degenerative arthritis) or the diseases of old age, a joint cavity filled with synovial fluid malfunctions, excessive friction or direct collision occurs between the articular cartilage of the thighbone and the meniscus of the shinbone, or the left and right sides of the knee cartilage are imbalanced, the knee joint is deformed or pain is caused. The conventional knee brace or protector has a drawback in that smooth rotation and shock absorbing action cannot be realized while the balance between the left and right sides of the knee cartilage is adjusted.

In the conventional knee protectors, a part performing the shock absorbing action is limited to the tubular body or the shaft inserted into the tubular body, so that the width of the shock absorbing part is narrow. Thus, flexural deformation caused by vertical moving force and twisting force of the body acts on the narrow tubular body or shaft. Hence, the part which performs the shock absorbing action of the knee joint and the subsidiary function of joint movement cannot stably support the upper cuff and the lower cuff.

Further, the conventional knee protectors are problematic in that a spring, which has a relatively shorter stroke distance in consideration of the load acting on the leg, or has a lower allowance in consideration of maximum tolerance compression height, so that the knee is overstrained.

Further, the conventional knee protectors are problematic in that shock absorbing action occurs only in the tubular body and the shaft inserted into the tubular body, so that shocks cannot be smoothly absorbed and the tubular body may be broken. The conventional knee protectors cannot overcome the low fatigue resistance of the spring, which absorbs shocks for a lengthy period of time, so that it is difficult to generate sufficient shock absorbing force, and durability is very low.

According to the prior art, the shaft inserted into the tubular body is integrated with the upper cuff. Thus, when a specific portion of the upper cuff is broken, the entire upper cuff must be separated from the lower cuff and be replaced with a new one. As such, the conventional knee protectors have a structural problem, and are inconvenient to maintain.

Further, according to the prior art, an upper or lower tightening part using a coil spring is provided to firmly secure the upper or lower cuff to the body. However, it is very complicated and inconvenient to manufacture the tightening part. The tightening part cannot closely correspond to the anatomical shape of the human body.

DISCLOSURE OF INVENTION

Technical Problem

Accordingly, the present invention has been made keeping in mind the above problems occurring in the prior art, and an object of the present invention is to provide an orthopedic knee joint brace, which is provided with a multiple pivot link structure and a damping structure to correspond to the movement of the knee joint, thus permitting smooth knee exercise, increasing the durability of a spring, ensuring structural rigidity in a shock absorbing operation, and compensating for the balance between the left and right sides of cartilage.

Technical Solution

In order to accomplish the object, the present invention provides an orthopedic knee joint brace having an upper cuff assembly having an anatomical shape of a thigh to support the thigh, and a lower cuff assembly provided under the upper cuff assembly to be spaced apart from the upper cuff assembly, the orthopedic knee joint brace including a pair of damping pivot assemblies coupling facing ends of both sides of the upper and lower cuff assemblies to each other, each of the damping pivot assemblies having a multiple pivot link structure and a guide damping structure to correspond to joint movement of a knee.

ADVANTAGEOUS EFFECTS

As described above, the present invention provides an orthopedic knee joint brace, which is capable of compensating for imbalance between the left and right sides of cartilage, in addition to functioning to relieve the pain and shocks of the knee joint.

Further, the orthopedic knee joint brace of the present invention has various swelling heights to correspond to the anatomical shape of the human body, and uses a plurality of plate springs having different magnitudes of elastic restoring force according to the strength of the muscles of the leg, so that the brace is in closer contact with the body, thus overcoming economical difficulties in the manufacture thereof, and aiding in promoting blood circulation.

Further, an orthopedic knee joint brace of the present invention vertically compresses or extends a spring provided in a pocket by a guide damping structure, and guides the vertical movement of the spring to a guide slot, thus being resistant to torsion force and realizing stable shock absorbing action.

Furthermore, an orthopedic knee joint brace of the present invention is designed to maintain fatigue resistance for a lengthy period of time so as to prolong the life-span of a spring, and is advantageous in that operating or sliding noise is small due to the shape characteristics of the pocket accommodating the spring and a movable part.

BEST MODE FOR CARRYING OUT THE INVENTION

A multiple pivot link structure, which is to be described in the description and claims of the present invention, has been invented by this inventor, who is a doctor and has cared for patients complaining of pain in the knee joints for several years. The multiple pivot link structure is constructed so that one end of each of the pivot links of a damping pivot assembly is hinged to a pivot rotator, the other end of each of the pivot links is hinged to a lower cuff of a lower cuff assembly, and the pivot rotator is fitted over a rotating protrusion of a movable frame, thus allowing the movable frame and the pivot rotator to have a stable coupling and support structure.

Such a multiple pivot link structure includes the plurality of pivot links of the damping pivot assembly, for example, a first pivot link, which serves as a bracket hinge, and a second pivot link, which serves as a 'V'-shaped plate link. The first pivot link and the second pivot link are hinged between the lower cuff and the pivot rotator. The rotation of the first pivot link is limited by the shape of the pivot rotator and the function of a guide and a stopper. Thereby, the multiple pivot link structure realizes stable rotation without overstraining the knee.

Further, a guide damping structure, which is to be described in the description and claims of the present invention, vertically compresses or extends a spring provided in a pocket to a movable part, so that the compression and the extension of the spring are repeated as in a general spring damping curve, thus absorbing shocks. The guide damping structure allows the movable part and the movable frame coupled via a guide shaft to slide along a guide slot of a plate guide positioned adjacent to the pocket.

According to the present invention, as the height of the damping pivot assembly, installed to an upper cuff, is adjusted using a height adjusting slot of the damping pivot assembly, the balance between the left and right sides of cartilage can be adjusted according to a patient's condition.

According to the present invention, the spring is designed to maintain fatigue resistance for a lengthy period of time. Preferably, the spring has a maximum tolerance compression height determined in consideration of the load of one leg, spring allowance, and the free height which is equal to the sum of upper and lower stroke distances when the spring is compressed or extended.

Further, the pocket of the present invention is designed to completely surround an actuating shaft provided on the upper end of the movable part, thus providing a good appearance and minimizing inconvenience due to the protrusion of the movable part during movement.

Further, a sealing structure or an integrated structure is provided on portions of the movable part and the pocket other than open portions where parts are inserted or coupled, thus reducing noise generated by the operation of the spring.

According to the present invention, parts on which the largest load acts, that is, the pocket, the spring, and the movable part, are manufactured as a single module, thus affording easy maintenance and replacement of a product.

Further, numerical values disclosed in the present invention are used merely to promote understanding of the product, but do not limit the present invention.

MODE FOR THE INVENTION

Hereinafter, the preferred embodiment of the present invention will be described in detail with reference to the accompanying drawings.

Figure 2:
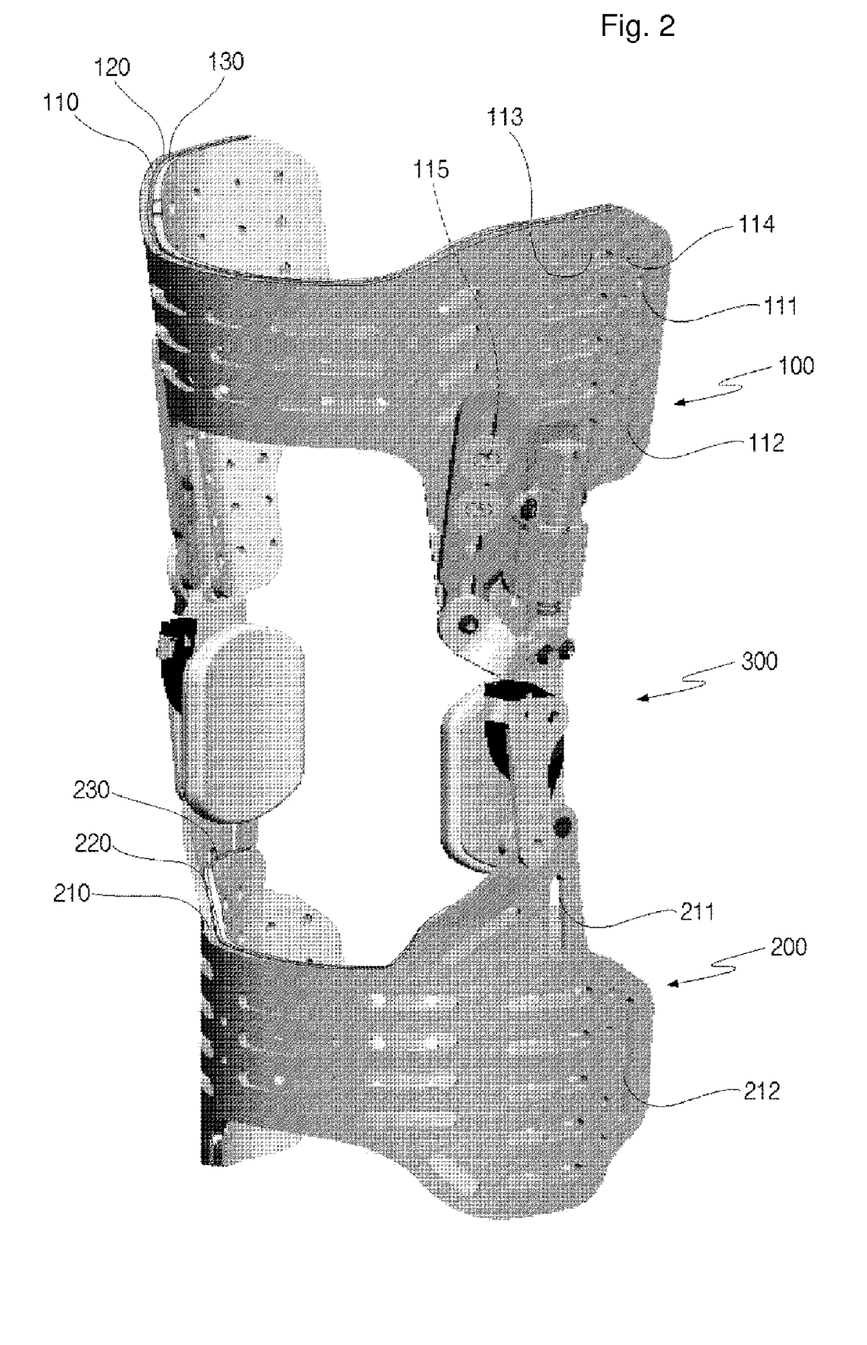
FIG. 2 is a perspective view illustrating the construction of an orthopedic knee joint brace, according to an embodiment of the present invention.

As shown in FIG. 2, the orthopedic knee joint brace of the present invention includes at least one upper cuff assembly 100, a lower cuff assembly 200 which is provided under the upper cuff assembly 100 and spaced apart from the upper cuff assembly, and a pair of damping pivot assemblies 300. The damping pivot assemblies 300 couple facing ends (e.g. the lower coupling portion of the upper cuff assembly and the upper coupling portion of the lower cuff assembly) of both sides of the upper and lower cuff assemblies 100 and 200 to each other, and have a multiple pivot link structure and a guide damping structure to correspond to the movement of the knee joint.

The upper cuff assembly 100 is provided right above the knee joint, and is worn around the thigh. The upper cuff assembly includes an upper cuff 110, an inner plate 120, an inner pad 130, and a plurality of belts (not shown). The upper cuff 110 has the shape of a curved plate which corresponds to the shape of the thigh. The inner plate 120 is curved to correspond to the curvature of the upper cuff 110. The inner pad 130 is curved to correspond to the curvature of the inner plate 120. The belts are fastened to both ends of the back surface of the upper cuff 110 to compress the thigh, and comprise Velcro fasteners so that the two ends of each belt are detachably fastened to each other.

The lower cuff assembly 200 is provided right under the knee joint, and is worn around the shinbone. The lower cuff assembly 200 has a lower cuff 210, an inner plate 220, an inner pad 230, and belts, which have the same shape as the upper cuff assembly 100 except that the lower cuff assembly corresponds to the shape of the shinbone.

Preferably, a plurality of belt fastening holes 111, 112, 211, and 212, having the shape of longitudinal holes, is formed in both ends of the back surface of each of the upper and lower cuff assemblies 110 and 210 so as to secure the belts.

The belts have different widths and lengths according to the size of the belt fastening holes 111, 112, 211, and 212 and the thickness of the leg. Preferably, a Velcro fastener is attached to both side ends of each belt.

Each of the upper and lower cuffs 110 and 210 is manufactured using a reinforced plastic material, such as glass fiber, carbon fiber, or Kevlar, so as to have a light weight, high durability, and firm rigidity and supporting force. Preferably, in order to secure rigidity, each of the upper and lower cuffs has a predetermined thickness (e.g.: 3t)(1t=1 mm), and has a plurality of air holes 113, a plurality of plate spring mounting holes 114 formed in consideration of the assembly tolerance of plate springs, and a plurality of assembly mounting holes 115 having the shape of a longitudinal hole extended transversely in consideration of the assembly tolerance of the damping pivot assemblies 300.

The position of each damping pivot assembly 300, installed between the upper cuff 110 and the lower cuff 210, is preferably set such that the pocket 320, the spring 330, and a movable part 340 correspond to an extrapolated line of knee movement.

Figure 3:
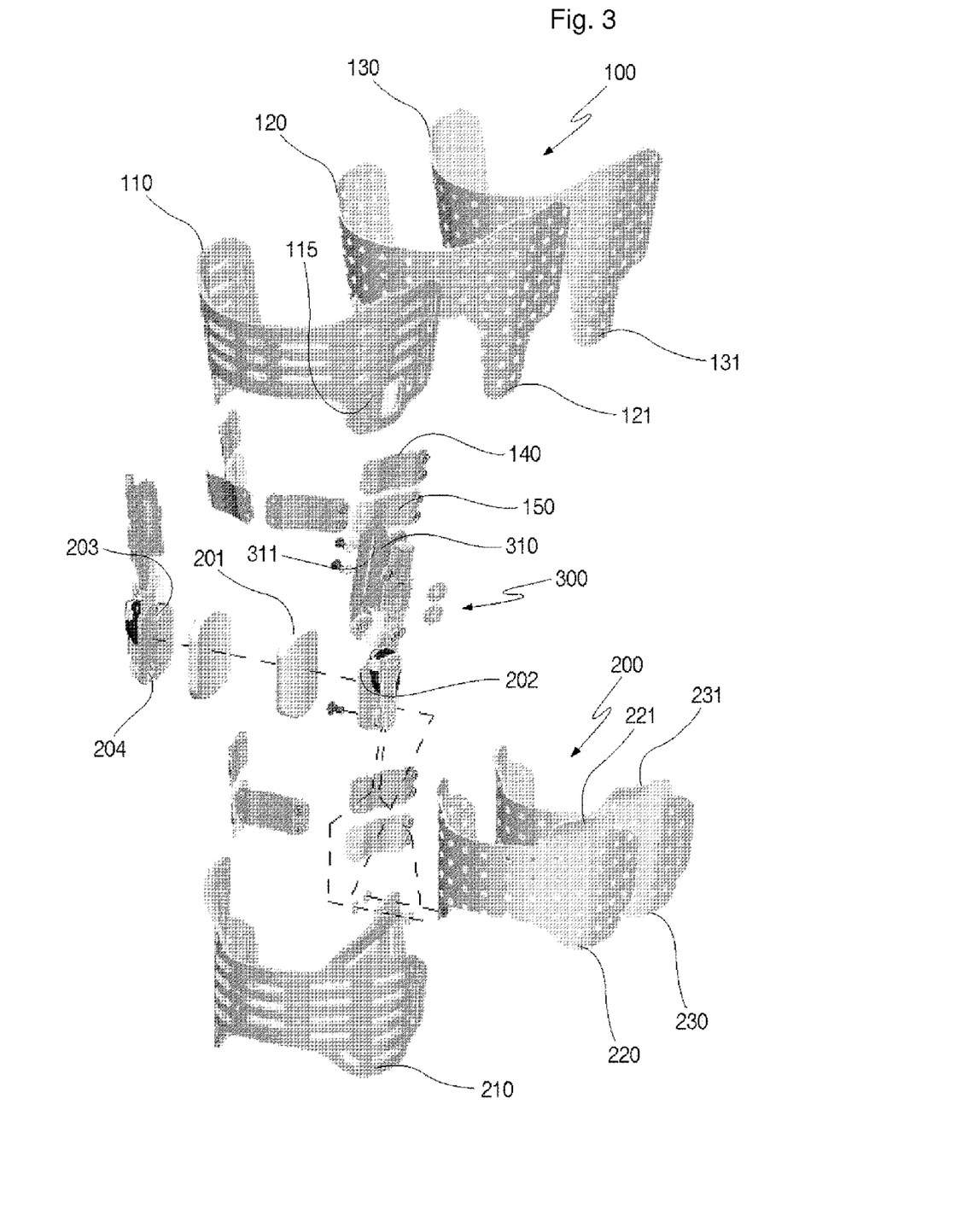
FIG. 3 is an exploded perspective view of the orthopedic knee joint brace shown in FIG. 2.

As shown in FIG. 3, preferably, each of the upper and lower cuffs 110 and 210 has no sharp edges, burrs, or cracks, and all of each of the upper and lower cuffs is treated in black coating after the manufacture thereof has been completed. Further, each of the upper and lower cuffs preferably goes through general surface treatment so as to prevent defective painting and prevent a coated surface from peeling off when it is in use.

Each of the inner plates 120 and 220 is superposed on the associated upper cuff 110 or lower cuff 210 after a plurality of plate springs 140 or 150 is placed on the inner surface of the associated upper cuff 110 or lower cuff 210. Each of the inner plates is made of a synthetic resin material, such as Acrylonitrile Butadiene Styrene (ABS), which has superior processability, high shock resistance, and high chemical resistance. It is preferable that each of the inner plates 120 and 220 have a predetermined thickness (e.g.: 1t) so as to uniformly transmit elastic force.

Preferably, each of the inner plates 120 and 220 has no sharp edges, burrs, or cracks, and has a plurality of air holes, plate spring mounting holes, and portions to which a fastening means, such as a Velcro fastener, is secured.

Further, each of the inner pads 130 and 230 is detachably placed on the inner surface of the associated inner plate 120 or 220 with a Velcro fastener interposed between each inner pad and the associated inner plate. Each of the inner pads is made of a material that is softer than that of the inner plates 120 and 220, or is made of a pad material, such as a general cushioning sheet. Preferably, each of the inner pads has a predetermined thickness (e.g.: 2t) so as to increase the contact sensation but eliminate a bumpy textured sensation.

Of course, the inner pads 130 and 230 have a plurality of air holes, like the inner plates 120 and 220. The inner pads are fastened to the inner plates using a Velcro fastener such that the air holes of the inner pads 130 and 230 are aligned with the air holes of the inner plates 120 and 220, thus improving air permeability and providing a good wearing feel.

Further, extension parts 121, 131, 221, and 231 are preferably provided on the inner pads 130 and 230 and the inner plates 120 and 220, so that the inner pad 130 and the inner plate 120 extend downwards to be lower than the upper cuff 110, and the inner pad 230 and the inner plate 220 extend upwards to be higher than the lower cuff 210, thus preventing a user's skin from being directly compressed.

Each damping pivot assembly 300 is provided between the upper and lower cuff assemblies 100 and 200, and serves to absorb or disperse shocks when the knee joint is moved.

Further, each damping pivot assembly 300 has a particular construction and coupling, thus firmly and stably performing pivot operation or rotation similar to joint movement, and compensating for imbalance between the left and right sides of cartilage according to the knee test result.

Preferably, each damping pivot assembly 300 has on an inner surface thereof a knee pad 201 so that the damping pivot assembly 300 is not in direct contact with the skin surrounding the knee.

The knee pad 201 is manufactured using a general cushioning material, such as silicone, sponge, or soft rubber, and preferably has a predetermined thickness (e.g.: 7t) to provide elastic force and touch which can sufficiently surround and protect the knee.

The knee pad 201 is detachably attached to a pad supporting cover 202 via a general fastening means, such as a Velcro fastener.

The pad supporting cover 202 is made of rubber or synthetic resin having mechanical hardness (e.g.: HV80) which is sufficient to support the knee pad 201, and has the shape of a curved plate. A plurality of coupling holes 203 and 204 is formed in the pad supporting cover so as to couple the pad supporting cover to each damping pivot assembly 300.

Each damping pivot assembly 300 is coupled to the upper cuff 110 using a height adjusting slot 311 formed in a plate guide 310, and the plurality of assembly mounting holes 115 of the upper cuff 110. While a plurality of hexagon bolts, nuts, and washers is fastened to the assembly mounting holes 115 and the height adjusting slot 311, the installation height of each damping pivot assembly 300 is adjusted relative to the upper cuff 110, thus compensating for imbalance between the left and right sides of cartilage.

Figure 4:
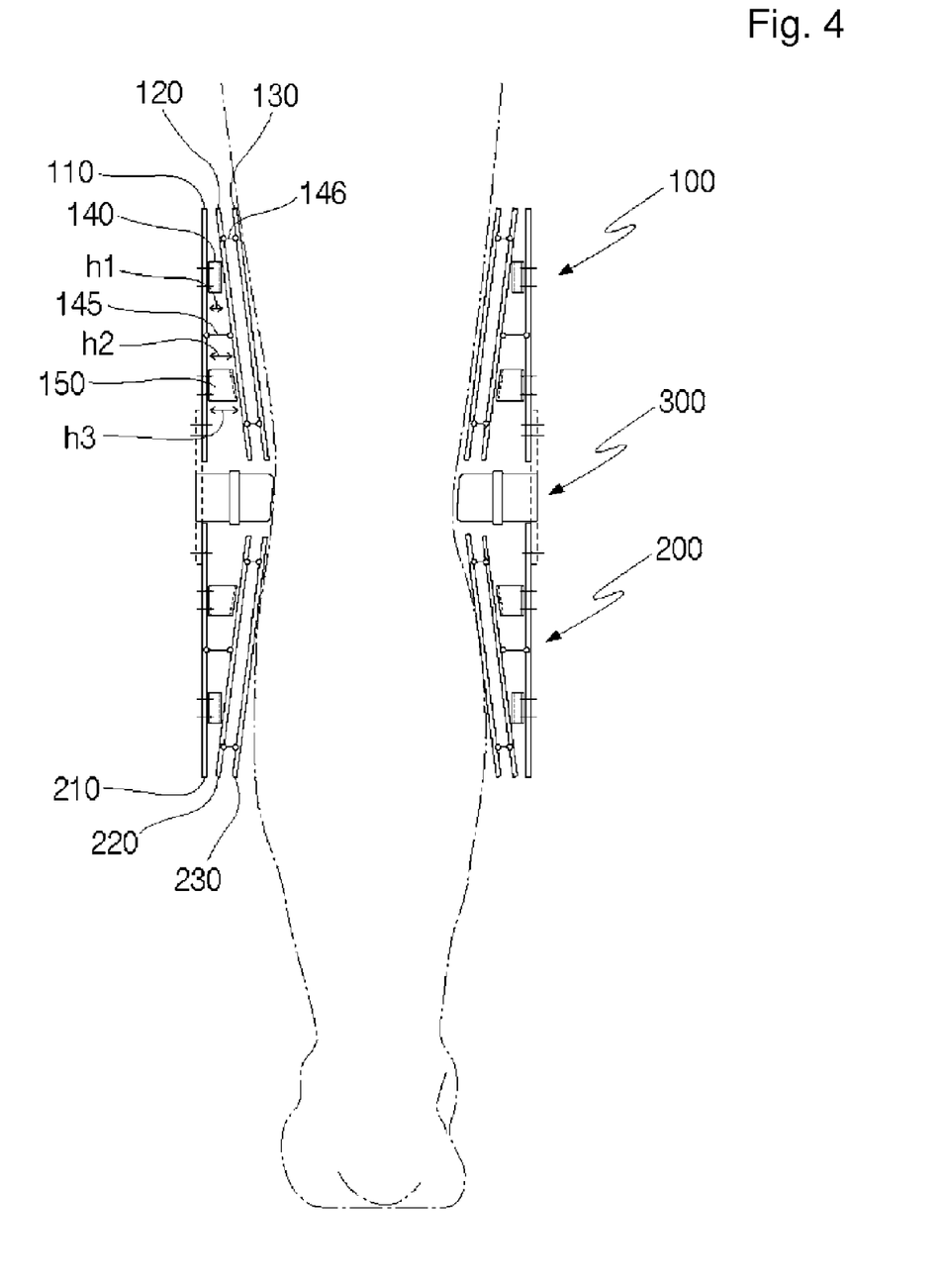
FIG. 4 is a schematic view illustrating the use of the orthopedic knee joint brace shown in FIG. 2.

The installation of the orthopedic knee joint brace according to the present invention will be described with reference to FIG. 4. The upper cuff assembly 100 is worn around the thigh region using belts, and the lower cuff assembly 200 is worn around the shinbone region using other belts. In this way, the damping pivot assemblies 300 are placed on both sides of the knee joint.

Particularly, in the upper cuff assembly 100 or the lower cuff assembly 200, a plurality of plate springs 140 and 150 is interposed between the upper cuff 110 and the inner plate 120 or between the lower cuff 210 and the inner plate 220, and has different swelling heights h1, h2, and h3 to correspond to the anatomical shape of the body and have different magnitudes of elastic restoring force according to the strength of the muscles of the leg.

For example, the plate springs installed around the thigh region will be described. That is, a plurality of plate springs 140 having a lower swelling height h1 is installed to the thicker portion of the leg (the thicker portion is the upper portion of the thigh or is the middle portion of the shinbone, and the circumference is larger than the knee joint).

Further, a plurality of plate springs 150 having higher swelling heights h2 and h3 is installed to the thinner portion of the leg (the thinner portion is the lower portion of the thigh or is the upper portion of the shinbone, and the circumference is smaller than the knee joint).

The plate springs 140 and 150 are made of a stainless steel material (e.g.: STS301). Each of the plate springs has the shape of a section such that both ends thereof are slightly inclined upwards and an upwardly swollen portion is provided between the ends.

In this case, a plurality of fastening holes is formed in both ends of the plate springs 140 or 150 so as to fasten the plate springs to the upper cuff 110 or the lower cuff 120.

Further, the reason why both ends of each plate spring 140 or 150 are inclined upwards is because both ends of each plate spring correspond to the swelling inclination of the upper or lower cuff assembly 100 or 200, and are thus in surface contact with the upper or lower cuff assembly. Further, each plate spring 140 or 150, which is in surface contact with the upper or lower cuff assembly, can generate precise elastic restoring force which corresponds to a design value.

Further, each of the plate springs 140 and 150 provides a new surface contact structure which air-tightly corresponds to the anatomical structure of a body part, thus allowing the upper or lower cuff assembly 100 or 200 to be firmly coupled to the body, and solving economical problems with the manufacture and assembly thereof.

When compared to a conventional belt fastening method or a conventional method, which is disclosed in Korean Patent Appln. No. 10-2005-0032044 and was invented by the same inventor, the plate springs 140 and 150 having different heights have a plurality of air holes on contact portions, thus permitting smoother blood circulation. The force compressing the upper cuff 110 or the lower cuff 120 is adjusted according to the elastic restoring force of the associated plate springs 140 or 150, thus maximizing the degree of contact.

A more preferable construction corresponding to the anatomical shape of the body is as follows. The plurality of plate springs 150 having high swelling heights h2 and h3 is formed to be inclined from one end having the swelling height h2 to the other end having the swelling height h3. Such a construction provides a natural wearing feel to a wearer, and improves the degree of contact according to the thickness of the leg.

Meanwhile, the upper cuff 110 and the inner plate 120 of the upper cuff assembly 100 may be coupled to each other through a bolt-nut coupling, a rivet coupling, or an eyelet coupling.

Further, after both ends of each plate spring 140 or 150 are coupled to the upper cuff 110, the upper cuff 110 and the inner plate 120 may be coupled to each other using a Velcro fastener 145, which is provided between the upper cuff and the inner plate.

Another Velcro fastener 145 is used to detachably attach the inner plate 120 and the inner pad 130 to each other.

The coupling of the lower cuff 210, the inner plate 220, the plate springs, and the inner pad 230 of the lower cuff assembly 200 is conducted in the same manner as the above-mentioned coupling of the upper cuff assembly 100.

Figure 5:
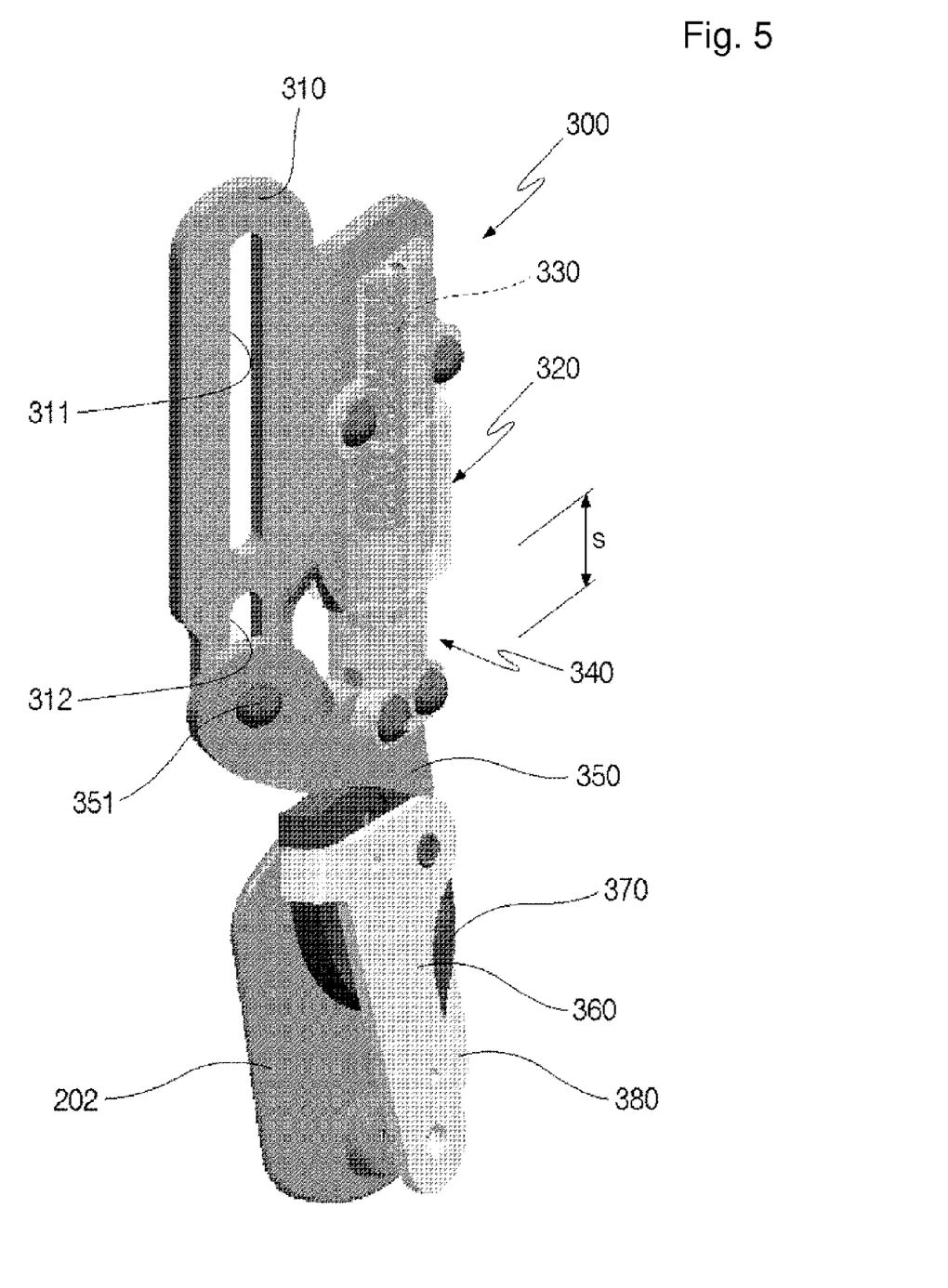
FIG. 5 is a perspective view of a damping pivot assembly shown in FIG. 2.

As shown in FIG. 5, each damping pivot assembly 300 has the plate guide 310, which is made of a reinforced plastic material and has a thickness of about 3t.

The height adjusting slot 311 is formed in one side of the plate guide 310 and is fastened to the upper cuff using a plurality of detachable hexagon bolts, nuts, and washers. A guide slot 312 is formed right under the height adjusting slot 311.

The height adjusting slot 311 has the shape of a longitudinal hole which is long in a vertical direction, thus serving as a coupling point for coupling each damping pivot assembly 300 with the upper cuff, and serving to adjust the installation position thereof.

Further, each damping pivot assembly 300 has a pocket 320 and a spring 330. The pocket is mounted to the other side (right side) of the plate guide 310, that is, a pocket mounting part which is opposite the height adjusting slot 311. The spring 330 is seated in an inner cavity which is open downwards from the pocket 320.

Further, the spring 330, the pocket 320, and the movable part 340 of each damping pivot assembly 300 may be substituted by a pneumatic spring, a damper, an elastic structure, or other equivalents.

For example, the spring 330 comprises a coil spring, and is directly related to shock absorbing force and durability.

The spring 330 has the following dimensions. The outer diameter of the spring is 8 to 13π, the diameter of a spring wire is 1.5π, the free height of the spring is 60 mm, the maximum tolerance compression HT is 36.5 mm, and the vertical stroke distance (s), corresponding to 25% of an elastic force of 15 kgf per spring, is 15 mm. Here, since the spring 330 is installed on each of a pair of damping pivot assemblies 300, the spring is designed to sustain 30 kg per leg.

Further, the spring 330 is twice as large as a conventional spring used in Korean Patent Appln. No. 10-2005-0032044. The spring may be designed to be twice as high as the conventional spring, thus permitting smooth knee motion even when the elastic force of the spring acts.

Particularly, the shape of the pocket 320 and the movable part 340 and the coupling of the spring 330 with the pocket and the movable part are determined so that the spring 330 stops at the position where the vertical stroke distance is 15 mm.

Further, each damping pivot assembly 300 includes the movable part 340 and a movable frame 350. The movable part 340 is provided in the cavity of the pocket 320 to bias the spring 330. The movable frame 350 is coupled to the base of the movable part 340, and has a guide shaft 351 to be inserted into the guide slot 312.

Each damping pivot assembly 300 includes a pivot rotator 370, a first pivot link 360, and a second pivot link 380. The back of the pivot rotator 370 is shaped such that the pivot rotator is fitted over a rotating protrusion of the movable frame 350. The pivot rotator has a stable coupling or support structure with the movable frame 350, and the overall shape of the pivot rotator is a fan shape. An upper step and a lower step are formed in the upper end and the lower end of a guide arc surface, respectively, so that the pivot rotator serves as a stopper. The first pivot link 360 serves as a bracket hinge which is coupled to the pivot rotator 370 to be operated as a hinge. The second pivot link 380 serves as a 'V'-shaped plate link which is coupled to the pivot rotator 370 to be operated as a hinge, thus having a multiple pivot link structure.

Figure 6:
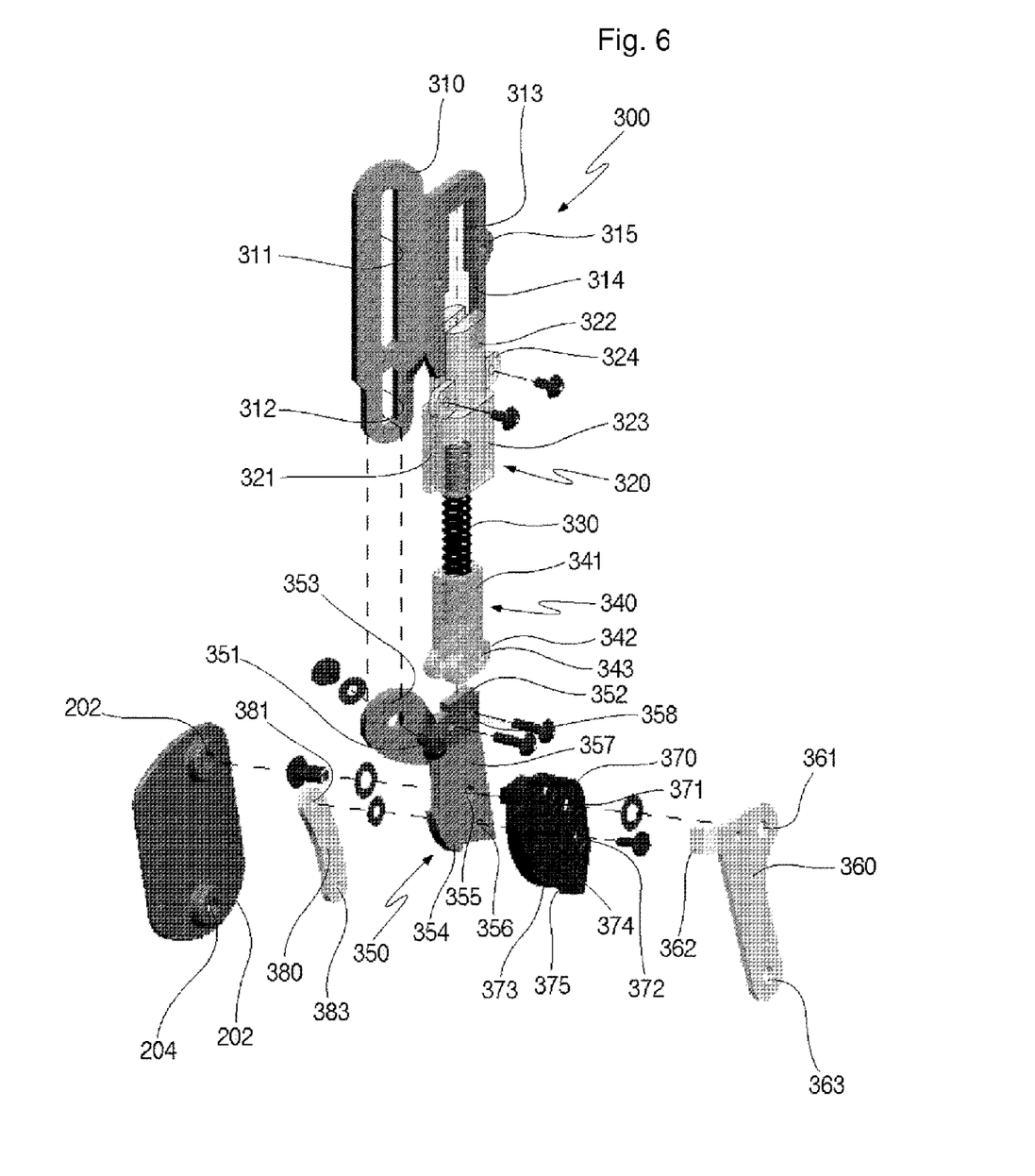
FIG. 6 is an exploded perspective view of the damping pivot assembly shown in FIG. 5.

As shown in FIG. 6, the plate guide 310 of the damping pivot assembly 300 has no sharp edges, burrs, or cracks, and the entire portion of the plate guide is treated in black coating after the manufacture thereof has been completed. Further, the plate guide preferably goes through general surface treatment so as to prevent defective painting and prevent a coated surface from peeling off when it is in use.

The plate guide 310 is bent so that one side and the other side thereof form a pre-determined angle (e.g.: 20 to 35°) therebetween. Thus, the plate guide is in close contact with the upper cuff, has high structural rigidity due to the bend angle, and is resistant to vertical buckling and torsion.

The pocket mounting part of the plate guide 310 includes a narrow slot 313, a wide slot 34 which is formed under the narrow slot and communicates with the narrow slot, and bolt holes 315 which are formed in both sides of the middle portion of the pocket mounting part.

The pocket 320, having fitting grooves 321 which correspond to the slots 313 and 314 and engage therewith, is slidably inserted into the slots 313 and 314.

The pocket 320 is formed using a nylon material (e.g.: nylon-66). No defective parts, such as contractions, weld lines, whitening, or burrs, are found in the appearance of the pocket.

The pocket 320 is a cylindrical casing having the shape of a multistage tower. In a detailed description thereof, the fitting grooves 321 are formed along both side edges and the upper edge of the pocket 320 so that the pocket is fastened to the slots 313 and 314 of the pocket mounting part of the plate guide 310, and the bottom of the pocket is open.

That is, the pocket 320 has an upper part 322 which is relatively narrower, a lower part 323 which is relatively wider, and ear parts 324 which are fastened to the bolt holes 315 of the plate guide 310 using bolts. The parts are integrated with each other, and are manufactured through injection molding.

Further, the cavity defined in the pocket 320 includes a narrow space and a wide space to correspond to the external appearance of the pocket 320, and a junction which serves as a stopper separating the narrow space from the wide space.

The spring 330 is inserted into the narrow space, defined in the upper portion of the cavity of the pocket 320 while maintaining a predetermined tolerance. Grease may be added in the space. An air vent hole (not shown) may be further formed at a pre-determined position along the extrapolated line of the spring in the pocket 320 or the movable part 340.

An upper actuating shaft 341 of the movable part 340 is inserted into the wide space of the lower portion of the cavity of the pocket 320 through the open hole, which is formed in the bottom of the pocket. In this case, the section of the open hole formed in the bottom is similar or equal to the section of the upper actuating shaft 341. Preferably, the sectional area of the open hole is slightly larger than the sectional area of the upper actuating shaft 341 by a predetermined tolerance.

After the insertion, the upper end of the upper actuating shaft 341 contacts the junction in the pocket 320 and is thus stopped.

Consequently, assuming that the vertical stroke distance of the spring 330 is set to be 15 mm, one of the vertical length of the upper portion of the movable part 340, the vertical depth of the wide space of the lower portion of the cavity in the pocket 320, and the distance from the open portion of the pocket 320 to the junction in the cavity is set to be 15 mm±tolerance.

As described above, the spring 330 has a maximum tolerance compression HT of 36.5 mm and a spring allowance value of 8.5 mm. When the upper actuating shaft 341 of the movable part 340 slides in the pocket 320, the vertical stroke distance is limited to correspond to the vertical stroke distance of the spring 330. Thus, even if a shock absorbing action has been performed for a lengthy period of time, the fatigue resistance of the spring is not reduced.

The movable part 340 has a base 342 which is integrally provided on the lower portion of the upper actuating shaft 341 having the shape of a hollow shaft, and is formed using the same material as the pocket 320.

The movable part 340 compresses or extends the spring 330 in the pocket 320 within a limited vertical stroke distance or a sliding distance range, like a kind of piston shaft, thus absorbing shocks.

In this case, the upper actuating shaft 341 of the movable part 340 has the shape of a hollow shaft which is open at the top thereof and is closed at the bottom thereof, thus serving as a spring seat on which the lower end of the spring 330 is seated.

The base 342, which is integrally provided on the lower portion of the upper actuating shaft 341, has the shape of a '∩', as seen from the side.

The '∩'-shaped base 342 has two legs and a horizontal part placed on the legs. The upper actuating shaft 341 is integrally provided on the horizontal part. In this case, a plurality of mounting holes 343 is formed in the base 342 to correspond to a plurality of extrapolated lines which connect the front and the back of the movable part 340 to each other.

Further, the base 342 of the movable part 340 has a depression on the bottom of the horizontal part which is provided between the two legs.

The depression of the base 342 of the movable part 340 is shaped such that a depression insert protrusion 352 of the movable frame 350 is fitted into the depression.

The movable frame 350 is the part which is made of a reinforced plastic material and has the thickness of 3t. The entire movable frame is treated in black coating. The movable frame 350 has a guide shaft 351 which is fastened to the guide slot 312 of the plate guide 310 so as to guide the vertical sliding operation of the movable part 340, in addition to supporting the base 342 of the movable part 340.

The movable frame 350 includes a frame extension part 353, the depression insert protrusion 352, and a frame body 357. The frame extension part 353 has a fastening hole, in which the guide shaft 351 is fastened, and is bent to face the guide slot 312 of the plate guide 310. The depression insert protrusion 352 protrudes upwards from the right side of the frame extension part 353. The frame body 357 includes the rotating protrusion 354, a first pivot hole 355, and a second pivot hole 356 under the depression insert protrusion 352.

Preferably, the depression insert protrusion 352 and the frame extension part 353 of the movable frame 350 are bent relative to the frame body 357 within a range which allows smooth assembly with corresponding parts and does not deteriorate functionality.

Here, the corresponding parts mean the base 342 of the movable part 340 with respect to the depression insert protrusion 352, and the part having the guide slot 312 of the plate guide 310 related to the frame extension part 353.

The coupling of the movable part 340 with the movable frame 350 will be described below.

The depression insert protrusion 352 of the movable frame 350 is inserted between the two legs of the base 342 of the movable part 340 and is fitted into the depression formed in the base. In this case, the plurality of mounting holes 343 (e.g.: two mounting holes) which are formed in the base 342 of the movable part 340 are aligned with mounting holes 358 which are formed in the movable frame 350. After the mounting holes 343 and 358 are aligned with each other, the movable part 340 and the movable frame 350 are fastened to each other using a fastening bolt or a speed rivet.

The pivot rotator 370 has an upper step 374 and a lower step 375, which are provided, respectively, on the upper end and the lower end of a guide arc surface 373.

The pivot rotator 370 is made of a nylon material (e.g.: nylon-66). No defective part, such as contraction, weld lines, whitening, and burrs, are found in the appearance of the pivot rotator.

The pivot rotator 370 is secured to surround part of the movable frame 350 around the rotating protrusion 354. A protrusion seating recess (not shown), surrounding the rotating protrusion 354 and the portion around the rotating protrusion, is formed in the back of the pivot rotator 370, and is fitted over the rotating protrusion 354.

When the protrusion seating recess engages with the rotating protrusion, two center holes 371 out of three holes of the pivot rotator 370 and a pair of multiple link holes 372 are aligned with the first pivot hole 355 and the second pivot hole 356 of the frame body 357, respectively.

Further, after the center holes 371 and the first pivot hole 355 are aligned with the coupling hole 203 formed in the pad supporting cover 202 and an upper coupling hole 361 of the first pivot link 360, the parts are coupled to each other in such a way as to be operated in the manner of a hinge, using a bearing washer, a collar-type fastening bolt, and a nut.

In this case, an 'L'-shaped stop end 362 of the first pivot link 360 is placed on the guide arc surface 373 between the upper and lower steps 374 and 375 of the pivot rotator 370. When the 'L'-shaped stop end 362 contacts either the upper step 374 or the lower step 375, the stop end functions to limit the rotation of the first pivot link 360 within a predetermined arc angular range.

Meanwhile, the second pivot link 380 is placed between the movable frame 350 and the pad supporting cover 202, with a bearing washer interposed between the second pivot link and the movable frame 350. In such a state, after an upper coupling hole 381 of the second pivot link 380 is aligned with the second pivot hole 356 of the movable frame 350 and the multiple link holes 372 of the pivot rotator 370, the parts are fastened to each other in such a way as to be operated in a hinge manner using a fastening means (e.g.: collar-type fastening bolt, nut, rivet).

Figure 7:
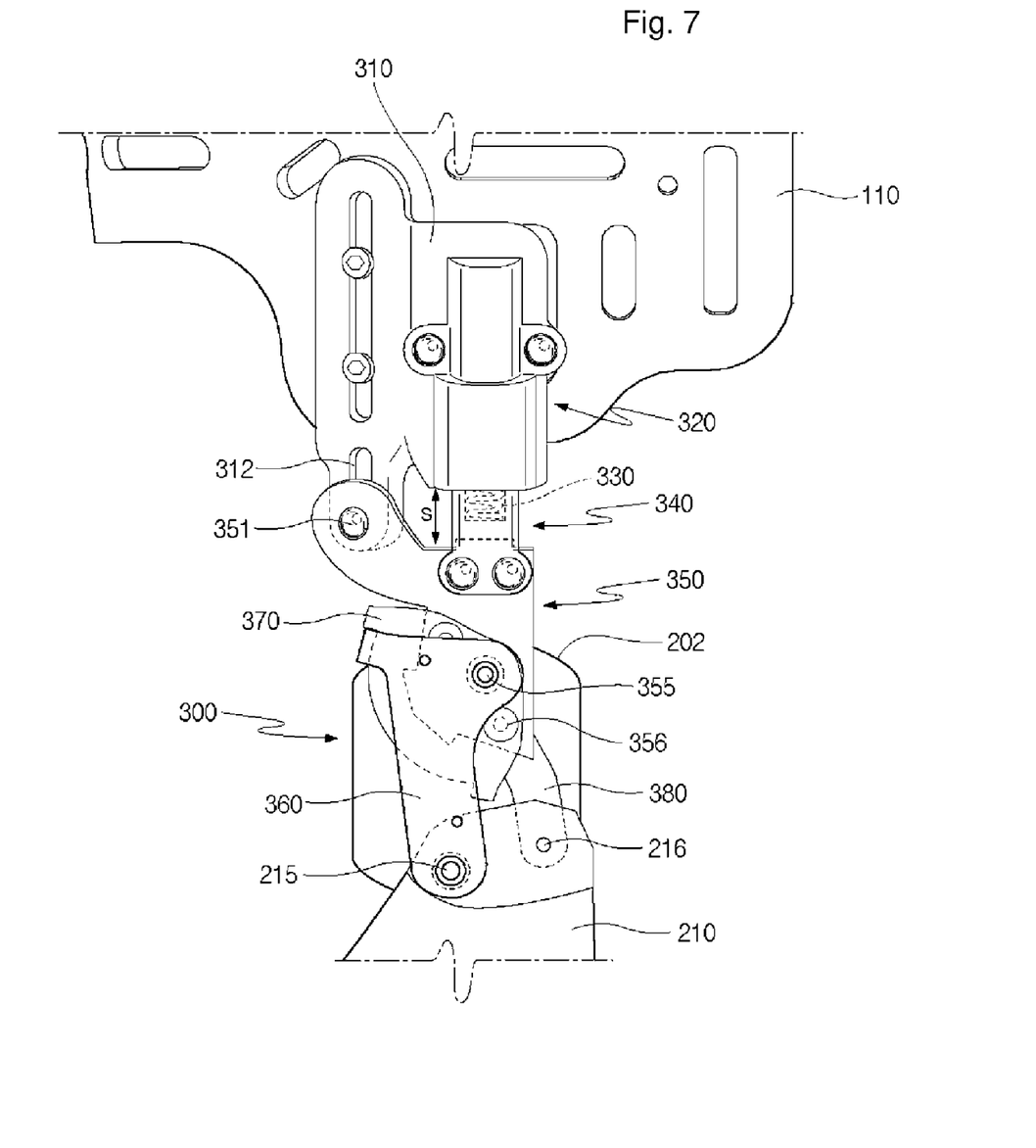
FIGS. 7 to 10 are side views illustrating the operation of the orthopedic knee joint brace, according to the present invention.
Figure 8:
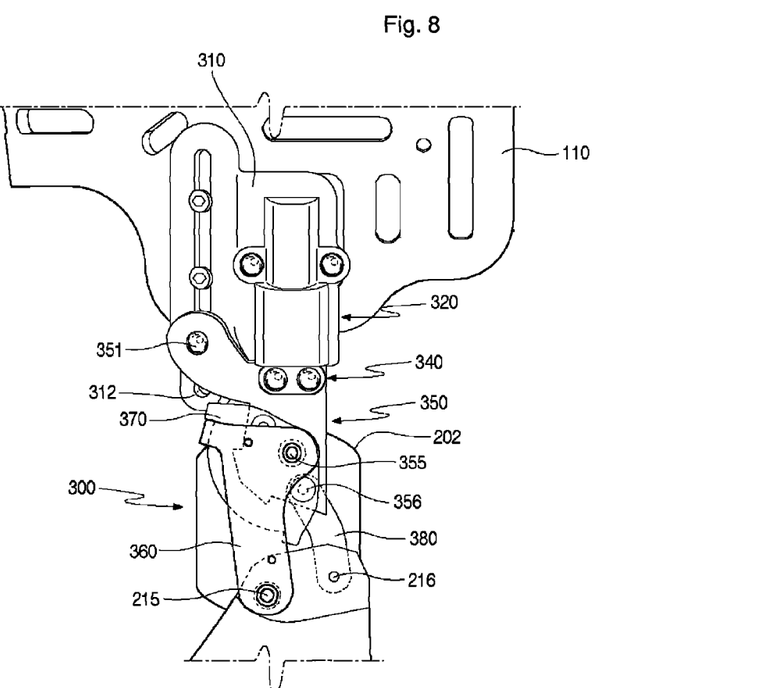
Figure 9:
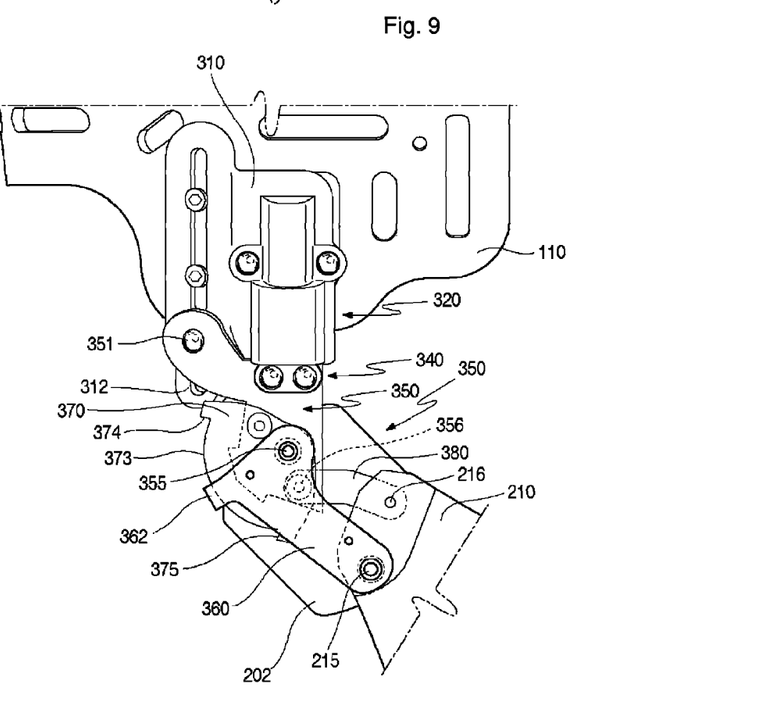

A lower coupling hole 363 of the first pivot link 360 and a lower coupling hole 383 of the second pivot link 380 are aligned with a third pivot hole 215 and a fourth pivot hole 216 of the lower cuff 210 (see, FIG. 3 or 7). The pivot links and the lower cuff are fastened to each other using a fastening means such that the lower portion of the damping pivot assembly 300 and the lower cuff 210 permit the hinge operation of the multiple pivot link structure.

For example, unlike the first pivot link 360, the second pivot link 380 has a 'V' shape, and a shorter straight length. Further, since the pivot position of the first pivot link and the pivot position of the second pivot link are staggered, the lower cuff 210 can be naturally and rapidly rotated when the second pivot link is rotated relative to the first pivot link 360.

The upper cuff 110, the lower cuff 210, the inner plates, and the inner pads have a plurality of air holes, and use the plate springs, generating different magnitudes of elastic restoring force according to the strength of the muscles of the leg, thus allowing blood to be smoothly circulated and allowing sweat to be smoothly discharged even when the brace is worn for a lengthy period of time.

Hereinafter, the operation of the orthopedic knee joint brace according to the present invention will be described in detail.

As shown in FIGS. 7 to 10, the knee joint brace of the invention is worn on the thigh and the shinbone, which are located above and under the knee joint. Afterwards, when the body bends or is moved, the damping pivot assembly 300, which is placed between the upper cuff 110 of the upper cuff assembly and the lower cuff 210 of the lower cuff assembly, performs shock absorbing action within a predetermined vertical stroke distance(s).

The shock absorbing action is actually performed in the pockets 320, the springs 330, and the movable parts 340. The movable frames 350, which slide up and down along with the movable parts 340, perform a parallel sliding motion while being guided by the plate guides 310.

These characteristics allow the upper cuff 110 and the lower cuff 210 to provide stable supporting force in spite of bend deformation caused by the vertical moving force and the body twisting force.

Further, the multiple pivot link structure of the present invention, including the first pivot link 360 and the second pivot link 380, which are coupled between the first to fourth pivot holes 355, 356, 215, and 216, allows the upper and lower cuffs 110 and 210 to be naturally bent or stretched relative to the damping pivot assembly 300 within a wider rotating range so as to correspond to the movement of the knee joint.

In particular, the pad supporting cover 202 equipped with the knee pad is rotated together when the first pivot link 360 rotates.

Figure 10:
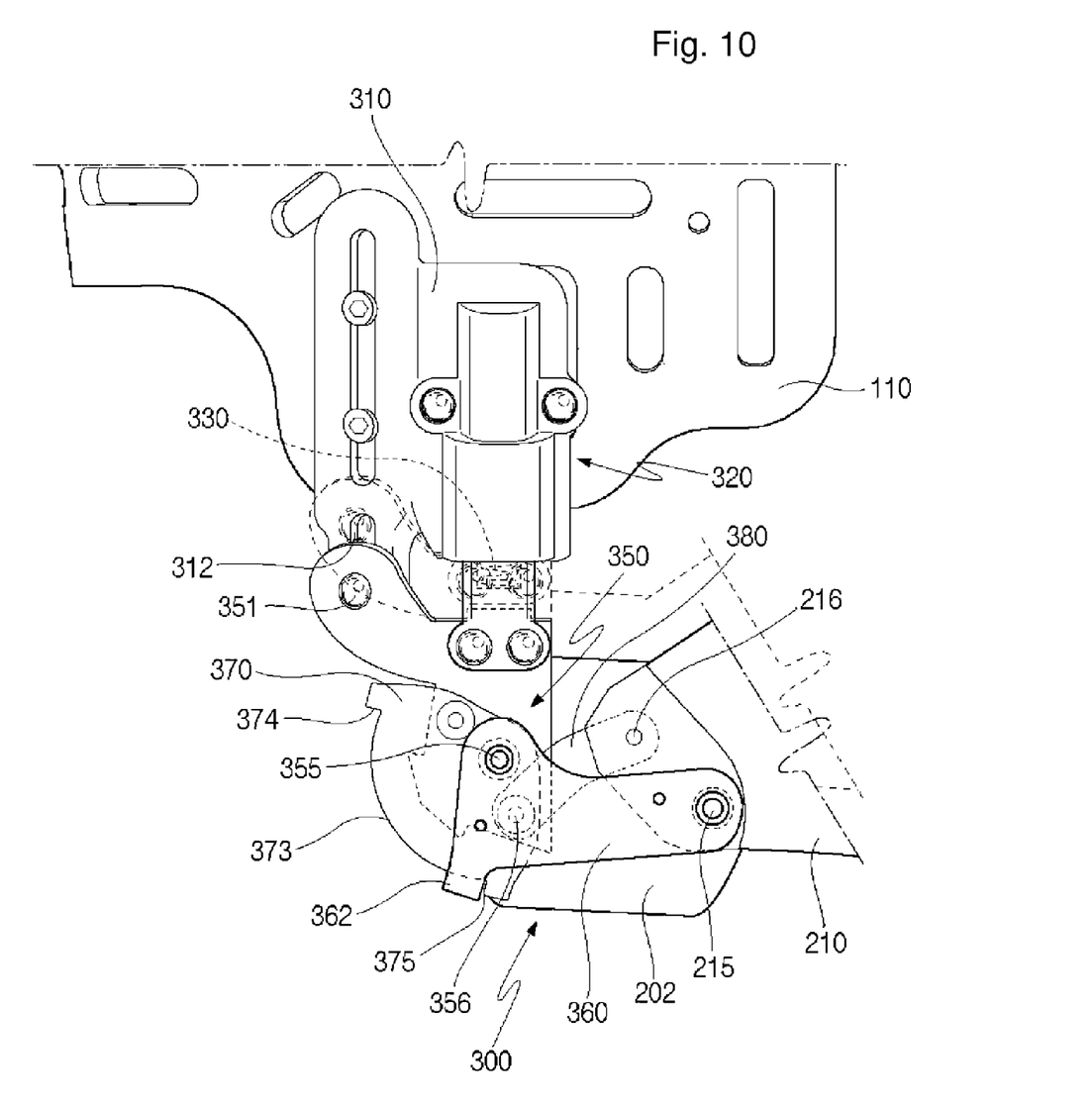

Preferably, a user (hereinafter referred to as a 'wearer') wearing the brace of the invention bends the lower cuff 210 at 90 degrees or more relative to the upper cuff 110 and the damping pivot assembly 300, as shown in FIG. 10. Further, the wearer maximally bends his or her leg and thereafter wears the brace of the invention using a band or the like.

When the wearer stretches his or her leg after wearing the brace in the above-mentioned manner, the thighbone can be more efficiently pushed up.

Particularly, when the wearer bends his or her knee at 90 degrees or more and lifts up the knee, the brace is bent such that the lower cuff 210 and the upper cuff 110 form the angle of 90 degrees or more.

In such a state, the guide shaft 351 of the movable frame 350 is positioned at the lower portion in the guide slot 312 of the plate guide 310, the spring 330 maintains a free height, and the movable part 340 is positioned at the bottom dead center of the vertical stroke distance of the pocket 320.

In such a state, when the wearer carefully walks on flat ground at a speed which is slower than a normal speed, a force or load which is two or three times as heavy as the wearer's weight may momentarily act on the knee or knee joint.

Particularly, when the wearer's leg is stretched in a straight line, so that a force which is two or three times as great as his or her weight, acts on the knee joint, the movable part 340 compresses the spring 330, and the upper actuating shaft of the movable part 340 is inserted into the pocket 320 within a limited range.

The movable frame 350 coupled to the movable part 340 stabilizes the direction of the acting support force while moving along the guide slot 312.

Further, the elastic force of the spring 330 attenuates the magnitude of the external force or performs shock absorbing action to mitigate shocks caused by the external force.

The damping pivot assembly 300, having such a spring 330, disperses the attenuated or mitigated external force through the upper cuff 110 or the lower cuff 210 to portions other than the knee joint, thus preventing the pain in the knee.

Afterwards, when the wearer stops moving or assumes a still posture, so that external force is not generated, the elastic force of the spring 330 acts as a kind of elastic restoring force, thus pushing up the pocket 320 and the upper cuff 110. The thighbone of the thigh, which is in close contact with the upper cuff 110, is spaced apart from the cartilage, thus minimizing friction and shocks on the knee cartilage.

Figure 11:
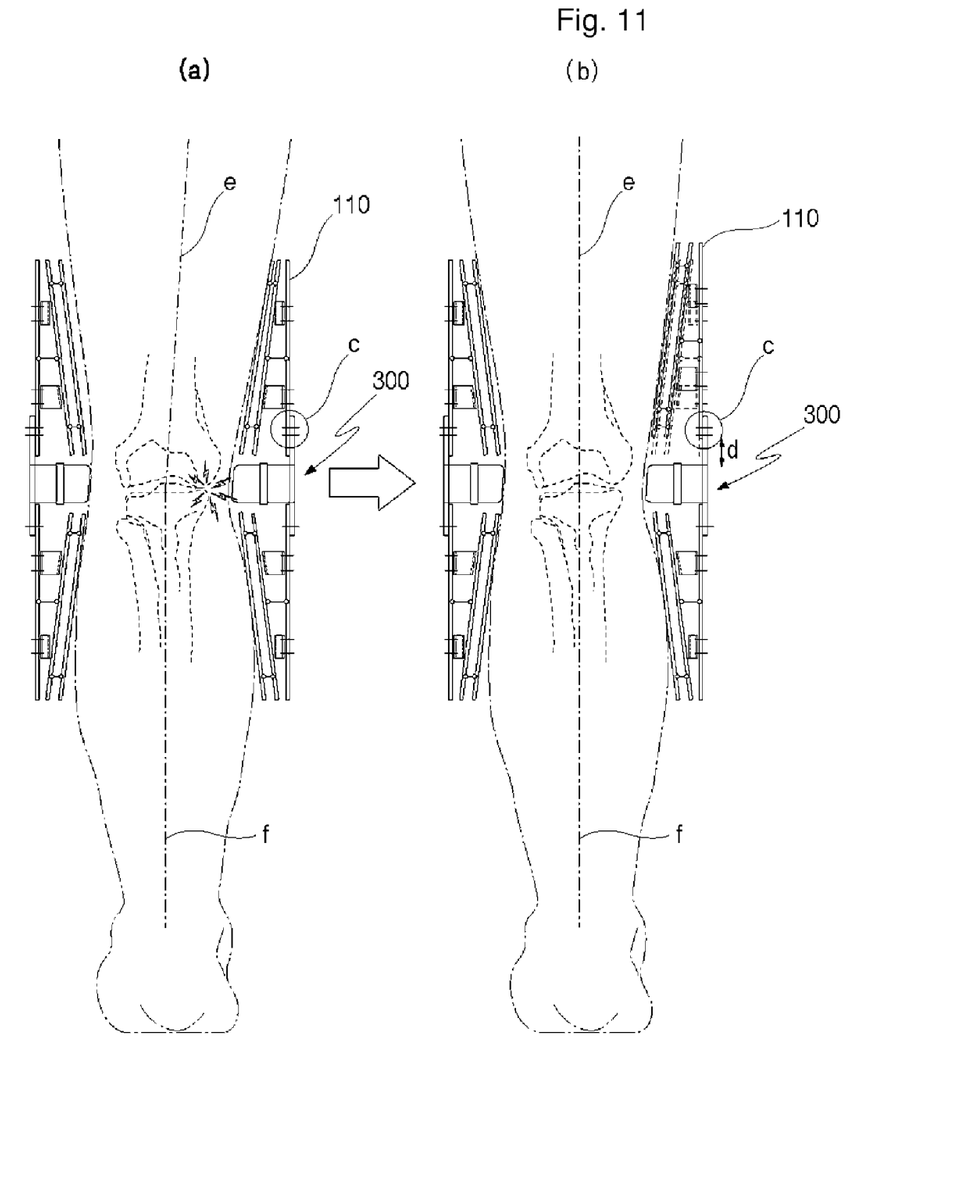
FIG. 11 is a front view illustrating the height adjustment of the damping pivot assembly installed to the orthopedic knee joint brace, according to the present invention.

Meanwhile, as shown in FIG. 11, a user (e.g.: orthopedic surgeon) helps the wearer adjust the balance between the left and right sides of the wearer's cartilage, based on the results of knee testing, when cartilage friction or pain occurs, like area a, corresponding to the left side of FIG. 11. Thereby, the balance between the left and right sides of the cartilage can be adjusted, like area b, corresponding to the right side of FIG. 11.

That is, the user slightly loosens a plurality of hexagon bolts and nuts in the assembly mounting hole of the upper cuff 110, as shown by circle C, according to the condition of the wearer's knee joint or cartilage. Thereafter, the user pushes up the upper cuff 110 or pushes down the damping pivot assembly 300 within the height adjusting slot in direction d, thus adjusting the installation height. Subsequently, the hexagon bolts or nuts are completely tightened, thus maintaining the firm coupling of the upper cuff 110 with the damping pivot assembly 300.

In this case, the central line e of the thighbone and the central line f of the shinbone are aligned in a row, thus compensating for the imbalance between the left and right sides of the cartilage.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As described above, the present invention provides an orthopedic knee joint brace, in which a pocket, a spring, and a movable part, on which the highest load acts, are manufactured into a single module, thus permitting easy maintenance and replacement of a product, and which uses a light and strong material, thus being superior as a medical device, and providing reliability and stability to a wearer, including a patient.

The invention claimed is:

1. An orthopedic knee joint brace having an upper cuff assembly having an anatomical shape of a thigh to support the thigh, and a lower cuff assembly provided under the upper cuff assembly to be spaced apart from the upper cuff assembly, the orthopedic knee joint brace comprising:
   a pair of damping pivot assemblies coupling facing ends of both sides of the upper and lower cuff assemblies to each other, each of the damping pivot assemblies having a multiple pivot link structure and a guide damping structure to correspond to joint movement of a knee,
   wherein each of the damping pivot assemblies comprises:
   a plate guide having in a first side thereof a height adjusting slot and a guide slot, and having on a second side thereof a pocket mounting part, the first and second sides being bent to be in close contact with the upper cuff;
   a pocket fitted into the pocket mounting part of the plate guide;
   a spring inserted into a cavity of the pocket;
   a movable part inserted into the cavity of the pocket to compress the spring;
   a movable frame coupled to a lower portion of the movable part, and guided by the guide slot of the plate guide;
   a pivot rotator shaped such that a back thereof is fitted over a rotating protrusion of the movable frame, and having a fan shape;
   a first pivot link hinged to a first pivot hole of the pivot rotator, and having an 'L'-shaped stop end located on a guide arc surface between an upper step and a lower step of the pivot rotator; and
   a 'V'-shaped second pivot link hinged to a second pivot hole of the pivot rotator.

2. The orthopedic knee joint brace according to claim 1, wherein each of the upper and lower cuff assemblies comprises:
   an upper cuff or a lower cuff made of a reinforced plastic material, and having a curved shape to correspond to the thigh or a shinbone region;
   an inner plate curved to correspond to a curvature of the upper cuff or the lower cuff, and made of a synthetic resin material;
   an inner pad curved to correspond to a curvature of the inner plate, and made of a softer material than the inner plate;
   a plurality of belts fastened to both ends of a back of the upper cuff or the lower cuff; and
   a plurality of plate springs installed between the upper or lower cuff and the inner plate, and having different magnitudes of elastic restoring force according to strength of muscles of a leg.

3. The orthopedic knee joint brace according to claim 1, wherein the multiple pivot link structure couples a first end of each of a plurality of pivot links of each damping pivot assembly to a pivot rotator via a hinge, couples a second end of each of the pivot links to the lower cuff of the lower cuff assembly via a hinge, and fits the pivot rotator over a rotating protrusion of a movable frame, thus providing a stable coupling and supporting structure to the pivot rotator and the movable frame.

4. The orthopedic knee joint brace according to claim 1, wherein the guide damping structure vertically compresses or extends a spring in a pocket using a movable part, and slides the movable frame coupled to the movable part and a guide shaft of the movable frame along a guide slot of a plate guide formed adjacent to the pocket, together with the movable part while maintaining the movable frame parallel to the movable part.

* * * * *